United States Patent [19]

Ose

[11] 4,436,734

[45] Mar. 13, 1984

[54] CONTROL OF SWINE DYSENTERY

[75] Inventor: Earl E. Ose, Greenfield, Ind.

[73] Assignee: Eli Lilly and Company, Indianapolis, Ind.

[21] Appl. No.: 458,381

[22] Filed: Jan. 17, 1983

[51] Int. Cl.³ .............................................. A61K 31/71
[52] U.S. Cl. ..................................... 424/181; 424/118
[58] Field of Search ................................. 424/118, 181

[56] References Cited

U.S. PATENT DOCUMENTS

| | | |
|---|---|---|
| 3,131,126 | 4/1964 | Gaeumann et al. ................. 435/131 |
| 3,947,586 | 3/1976 | Messersmith . |
| 4,027,034 | 5/1977 | Messersmith . |
| 4,185,091 | 1/1980 | Knusel et al. ........................ 424/118 |
| 4,291,053 | 9/1981 | Dost et al. . |

*Primary Examiner*—Sam Rosen
*Attorney, Agent, or Firm*—Leroy Whitaker; Arthur R. Whale

[57] ABSTRACT

The antibiotic, avilamycin, is useful in the treatment or prevention of swine dysentery.

9 Claims, No Drawings

CONTROL OF SWINE DYSENTERY

BACKGROUND OF THE INVENTION

Swine dysentery has plagued swine producers for many years and cost them millions of dollars annually. The disease is characterized pathologically by marked inflammation of the colon and cecal mucosa and clinically by dehydration, loss of body weight, and usually a mucohemorrhagic diarrhea. One of the major causes of swine dysentery appears to be *Treponema hyodysenteriae*.

Many chemotherapeutic agents and antibiotics have been evaluated for their prophylactic or therapeutic effectiveness against swine dysentery. Arsenic compounds such as arsanilic acid were among the first compounds found to be effective in the United States. However, animals treated with effective levels of arsenicals develop signs of arsenic poisoning. Sulfonamides and nitrofurans have shown limited efficacy. Antibiotics such as bacitracin, penicillin, streptomycin, chlortetracycline, oxytetracycline, and tylosin have been used with some effectiveness.

U.S. Pat. No. 4,027,034 discloses and claims a method for the prevention of swine dysentery by the oral administration of the antibiotic, monensin, to swine susceptible to the disease. Salinomycin is also said to be effective in the treatment of swine dysentery in U.S. Pat. No. 4,291,053.

The preparation of the antibiotic, avilamycin, is described in U.S. Pat. No. 3,131,126. In U.S. Pat. No. 4,185,091, avilamycin is said to be useful for promoting the growth of domestic animals when it is included in the feed for such animals. Swine are among the animals whose growth is said to be improved by the administration of avilamycin.

SUMMARY OF THE INVENTION

I have now discovered a method for the treatment or prevention of swine dysentery by the oral administration of an effective amount of avilamycin to swine suffering from or susceptible to swine dysentery. The availamycin may be conveniently administered to the animals in the feed or drinking water.

DESCRIPTION OF THE PREFERRED EMBODIMENT

Avilamycin is a known antibiotic, the preparation of which is described in U.S. Pat. Nos. 3,131,126 and 4,185,091, both of which are incorporated herein by reference.

In accordance with my method, swine suffering from swine dysentery are treated with avilamycin at a dosage of from about 5 to about 25 mg. per kg. of body weight per day. Avilamycin is conveniently administered to the animals in the feed or drinking water. When administered in the feed, avilamycin is added to the feed in an amount of from about 100 to about 500 g. of avilamycin per ton of feed. When administered in the drinking water, avilamycin is added to the water in an amount of about 0.2 to about 1 g. per gallon of water.

My method is also useful prophylactically to prevent swine dysentery or to reduce the severity of any infection that might occur. When used prophylactically in this manner, avilamycin is administered at a dosage of from about 1 to about 5 mg. per kg. of body weight per day. This dosage range is achieved by adding avilamycin to the feed in an amount of from about 20 to about 100 g. of avilamycin per ton of feed. Avilamycin may also be administered prophylactically in the animals drinking water by adding avilamycin to the water in an amount of from about 0.04 to about 0.2 g. of avilamycin per gallon of water.

The in vitro activity of avilamycin against *Treponema hyodysenteriae*, the primary agent of swine dysentery, was determined in a medium of 5% sheep blood agar. Concentrations of the avilamycin were tested ranging from 62.5 mg. per ml. of agar down to 0.78 mg. per ml. of agar. To each agar plate containing avilamycin was added a 0.1 ml. inoculum of a broth suspension of *Treponema hyodysenteriae* and the plates were incubated for three days under anaerobic conditions. Avilamycin was found to be active against *T. hyodysenteriae* at concentrations as low as 7.8 mg. per ml.

The following examples illustrate the use of avilamycin for the prevention of swine dysentery.

EXAMPLE 1

Forty-eight healthy weaned pigs were obtained from a commercial herd. They were identified by ear band and weighed individually. Eight groups of six pigs each were formed so that each group had the same mean pig weight. Each group was placed in an isolation room. Two of the groups were fed feed containing avilamycin at a level of 10 ppm., two groups were fed avilamycin at 20 ppm. and two groups were fed avilamycin at 40 ppm. The remaining two groups were given non-medicated feed. Five days after treatment with avilamycin was begun, each pig was challenged orally with 5 ml. of a colon tissue saline suspension prepared from two pigs with swine dysentery. The inoculum was cultured for salmonella.

The pigs were observed daily for diarrhea. Any pig that died was necropsied and the cause of death determined. The colon lesions of the necropsied pigs were recorded. Spleen, lymph node and colon tissue and contents were cultured for salmonella. The pigs were weighed individually every seventh day beginning the day of challenge. All pigs were subjected to necropsy examination as described above on the twenty-sixty day following challenge.

Salmonella was not found in the inoculum or from any of the tissues of the pigs at necropsy. Avilamycin was effective in a dose-related manner for the prevention of swine dysentery. Avilamycin levels of 20 and 40 ppm. resulted in a reduction in the number of pigs that died and marked improvement in weight gain. The 40 ppm. level was effective in reducing the incidence of colon lesions and in delaying and reducing the severity of diarrhea. The data collected in the experiment are summarized in Table I with the data reported being either the sum of the two groups at each treatment level or the average for the two groups as appropriate.

TABLE I

| Dose Rate | No. Deaths/ No. in Group | Avg. Gain[1] (lbs.) | No. with Lesions/ No. Examined | Days with Diarrhea |
|---|---|---|---|---|
| 0 | 5/12 | 3.3 | 9/12 | 20.0 |
| 10 ppm | 4/12 | 9.6 | 10/12 | 17.5 |
| 20 ppm | 2/11[2] | 15.6 | 9/11 | 10.0 |
| 40 ppm | 0/12 | 21.8 | 2/12 | 15.5 |

[1] Average gain per pig from day of challenge to termination of the experiment - 26 days
[2] One pig was removed from this group early in the experiment due to a severe leg problem unrelated to the treatment.

EXAMPLE 2

The procedure used in this example was the same as that used in Example 1 except for the level of avilamycin fed to the animals and the size of the challenge inoculum. Avilamycin was fed at levels of 50, 75 and 100 ppm, while the challenge was with 10 ml. of a colon tissue inoculum. All surviving pigs in this experiment were necropsied on the twenty-seventh day following challenge.

As in Example 1, salmonella was not found in the inoculum or from any pig at necropsy. Avilamycin did not appear to be effective at the 50 ppm level in controlling swine dysentery in this experiment. At both the 75 and 100 ppm levels, avilamycin was essentially equally effecting in controlling swine dysentery. However, control was not complete in that one of the pigs treated with avilamycin at the 100 ppm level died and was found to have mucus and hemorrhage in the colon. Weight gain for each of these treated groups was almost three times greater than that of the non-medicated, infected controls. The colons of twenty-one of the twenty-four pigs treated at either 75 or 100 ppm avilamycin were normal. In addition, these two levels of avilamycin markedly reduced the number of days in which mucus or blood was observed in the feces compared to the non-medicated, infected controls. The data from this experiment are summarized in Table 2.

TABLE II

| Dose Rate | No. Deaths/ No. in Group | Avg. Gain (lbs.) | No. with Lesions/ No. Examined | Days with Diarrhea |
|---|---|---|---|---|
| 0 | 3/12 | 10.75 | 10/12 | 18.5 |
| 50 ppm | 4/12 | 16.85 | 10/12 | 15.5 |
| 75 ppm | 0/12 | 20.8 | 1/12 | 0.5 |
| 100 ppm | 1/12 | 21.65 | 2/12 | 5 |

I claim:
1. A method for the treatment or prevention of swine dysentery which comprises administering to swine suffering from or exposed to swine dysentery an effective amount of avilamycin.
2. A method as in claim 1 wherein the swine are suffering from swine dysentery.
3. A method as in claim 2 wherein the avilamycin is administered at a dosage of from about 5 to about 25 mg. of avilamycin per kg. of body weight of the swine per day.
4. A method as in claim 3 wherein the avilamycin is administered in the swine's feed at a level of from about 100 to about 500 g. of avilamycin per ton of feed.
5. A method as in claim 3 wherein the avilamycin is administered in the swine's drinking water at a level of from about 0.2 to about 1 g. of avilamycin per gallon of water.
6. A method as in claim 1 wherein the swine are exposed to swine dysentery.
7. A method as in claim 6 wherein the avilamycin is administered at a dosage of from about 1 to about 5 mg. of avilamycin per kg. of body weight of the swine per day.
8. A method as in claim 7 wherein the avilamycin is administered in the swine's feed at a level of from about 20 to about 100 g. of avilamycin per ton of feed.
9. A method as in claim 7 wherein the avilamycin is administered in the swine's drinking water at a level of from about 0.04 to about 0.2 g. of avilamycin per gallon of water.

* * * * *